US011579083B2

(12) United States Patent
Ordonez Orellana et al.

(10) Patent No.: US 11,579,083 B2
(45) Date of Patent: Feb. 14, 2023

(54) IMPLANTABLE OPTICAL SENSOR

(71) Applicant: Indigo Diabetes N.V., Zwijnaarde (BE)

(72) Inventors: Juan Sebastian Ordonez Orellana, Ghent (BE); Danaë Delbeke, Gentbrugge (BE); Koenraad Van Schuylenbergh, Vorselaar (BE); Paolo Cardile, Ghent (BE); Ananth Subramanian, Mariakerke (BE)

(73) Assignee: Indigo Diabetes N.V., Zwijnaarde (BE)

( * ) Notice: Subject to any disclaimer, the term of this patent is extended or adjusted under 35 U.S.C. 154(b) by 639 days.

(21) Appl. No.: 16/500,098

(22) PCT Filed: Mar. 30, 2018

(86) PCT No.: PCT/EP2018/058347
§ 371 (c)(1),
(2) Date: Oct. 2, 2019

(87) PCT Pub. No.: WO2018/185033
PCT Pub. Date: Oct. 11, 2018

(65) Prior Publication Data
US 2020/0187832 A1 Jun. 18, 2020

(30) Foreign Application Priority Data

Apr. 3, 2017 (EP) .................................... 17164562

(51) Int. Cl.
*G01N 21/552* (2014.01)
*G02B 6/12* (2006.01)
(Continued)

(52) U.S. Cl.
CPC ....... *G01N 21/552* (2013.01); *G02B 6/12004* (2013.01); *A61B 5/1459* (2013.01);
(Continued)

(58) Field of Classification Search
None
See application file for complete search history.

(56) References Cited

U.S. PATENT DOCUMENTS

| 4,532,150 A | 7/1985 | Endo et al. |
| 5,880,552 A * | 3/1999 | McGill ............. G01N 29/2462 310/313 R |

(Continued)

FOREIGN PATENT DOCUMENTS

| JP | 2012-107901 A * | 6/2012 |
| WO | 2011/029886 A1 | 3/2011 |

OTHER PUBLICATIONS

Ana Belén González Guerrero, "Bimodal waveguide interferometer device based on silicon photonics technology for label-free and high sensitive biosensing", 2012.

(Continued)

*Primary Examiner* — Michael Stahl
(74) *Attorney, Agent, or Firm* — N.V. Nederlandsch Octrooibureau

(57) ABSTRACT

An implantable optical sensor (1) comprising a substrate (2) and at least one optical microstructure (3) for evanescent field sensing integrated with the substrate (2), the at least one optical microstructure (3) being positioned to form an optical interaction area (4) on a part of a surface (5) of the substrate (2), the optical assembly (1) further comprising a thin protective layer (6) covering at least the optical interaction area (4), the thin protective layer (6) being in a predetermined material with corrosion-protection characteristics and having a predetermined thickness, so as not to affect the evanescent field sensing.

16 Claims, 2 Drawing Sheets

(51) Int. Cl.
    *A61B 5/145*     (2006.01)
    *A61B 5/1459*     (2006.01)
    *G02B 6/13*     (2006.01)

(52) U.S. Cl.
    CPC ....... *A61B 5/14532* (2013.01); *A61B 2562/12* (2013.01); *A61B 2562/18* (2013.01); *A61B 2562/223* (2013.01); *G02B 6/13* (2013.01); *G02B 2006/12038* (2013.01); *G02B 2006/12061* (2013.01); *G02B 2006/12078* (2013.01); *G02B 2006/12138* (2013.01)

(56) References Cited

U.S. PATENT DOCUMENTS

| | | | |
|---|---|---|---|
| 6,332,363 B1 * | 12/2001 | Molloy | G01N 33/54373 73/776 |
| 7,087,887 B1 * | 8/2006 | Pi | G02B 6/2826 250/227.24 |
| 2002/0085204 A1 * | 7/2002 | Elkind | G01N 21/553 356/445 |
| 2006/0251357 A1 | 11/2006 | Dietrich et al. | |
| 2007/0081758 A1 | 4/2007 | Tono et al. | |
| 2009/0206242 A1 * | 8/2009 | Mizaikoff | G01N 21/7703 385/131 |
| 2010/0016928 A1 | 1/2010 | Zdeblick et al. | |
| 2011/0090484 A1 | 4/2011 | Osterlund et al. | |
| 2012/0170023 A1 * | 7/2012 | Szobota | G01N 21/552 356/51 |
| 2012/0226118 A1 | 9/2012 | Delbeke et al. | |
| 2016/0103065 A1 | 4/2016 | Lee et al. | |
| 2017/0038298 A1 * | 2/2017 | Morita | G01N 21/554 |

OTHER PUBLICATIONS

Zinoviev et al., "Silicon Photonic Biosensors for Lab-on-a-Chip Applications", Hindawi Publishing Corporation Advances in Optical Technologies, vol. 2008, Article ID 383927, 6 pages, doi:10.1155/2008/383927.

Oliveros et al., "Silicon carbide: a versatile material for biosensor applications", Biomed Microdevices (2013) 15:353-368, DOI 10.1007/s10544-013-9742-3, Published online: Jan. 15, 2013, Springer Science+Business Media New York 2013.

Janotta et al., "Analysis of Corrosion Processes at the Surface of Diamond-Like Carbon Protected Zinc Selenide Waveguides", Langmuir 2004, 20, 8634-8640, School of Chemistry and Biochemistry, Georgia Institute of Technology, Atlanta, Georgia 30332-0400, Institute of Chemical Process Development and Control, Joanneum Research, Steyrergasse 17, A-8010 Graz, Austria, and Laser Center Leoben, Joanneum Research, Leobner Strasse 94, A-8712 Niklasdorf, Austria.

"BD772 silicon carbide anti corrosion wear resistant coatings", Xiangyang City Hundred Shield Coating Material Co., Ltd, http://www.wearcoating.com/, jimmy@realbond.net.

* cited by examiner

IMPLANTABLE OPTICAL SENSOR

FIELD OF THE INVENTION

The present invention relates to an optical assembly comprising a substrate and at least one optical microstructure integrated with the substrate. The optical microstructure is positioned to form an optical interaction area on a part of a surface of the substrate. In a further aspect, the present invention relates to a method of manufacturing an optical assembly.

BACKGROUND ART

International patent publication WO2011/029886 discloses a sensor, sensing a substance such as glucose. The sensor is implantable in the body of a living creature. The sensor comprises a photonic integrated circuit, e.g. a silicon photonics based radiation processor for spectrally processing a radiation interacting with a sample.

US 2006/0251357 A1 discloses an optical component which contains a waveguide structure and a coupling element for the optical coupling of the waveguide structure to a further optical component. The waveguide structure and the coupling element are attached on a common substrate. The coupling element contains a reflecting, curved surface for the simultaneous change of the propagation direction and of the shape of the wave fronts of light which propagates between the waveguide structure and the optical components. Embodiments are described with a cover layer, which serves to protect the light-guiding core layer and the coupling element from external influences such as contamination, humidity or damage, and for optically insulating it from the surroundings. Typical thicknesses of the cover layer in the cured condition lie between 10 µm and 500 µm.

US 2007/0081758 A1 discloses an optical waveguide type biochemical sensor chip which includes a light beam transmittable substrate having at least a first optical element that allows a light beam to be impinged to the inside and a second optical element that emits a light beam from the inside, an optical waveguide layer that is formed on a main surface of the substrate on which at least one of the first and second optical elements is formed, has a thickness of 3 to 300 µm and is made of a polymer resin material having a higher refractive index than that of the substrate material, and a sensing membrane that is formed on the optical waveguide layer and creates a reaction product having the ability of absorbing the light beam or an evanescent wave of the light beam in response to an introduced specimen. The sensing membrane is formed in a region which is positioned between gratings and in which no protective film is formed.

US 2010/0016928 A1 discloses an implantable integrated circuit structure, e.g., an integrated circuit (IC) chip, an implantable pulse generator, a device with a multiplicity of IC chips where one chip contains electronic circuits and another chip has an optical sensor or emitter, etc. The structure comprises a conformal thin-film sealing layer for hermetically sealing circuitry layers. The sealing layer is a thin-film coating in that its thickness is such that it does not substantially increase the total volume of the structure with which it is associated. A thickness in a range from about 0.1 to about 10.0 µm is disclosed.

US 2016/0103065 A1 discloses an authentication apparatus for authenticating an object includes an input coupler configured to receive incident light and generate surface plasmons from the incident light; and an output coupler configured to output a speckle pattern based on the surface plasmons. The authentication apparatus includes a multi-layer structure comprising a metal film and a dielectric film. The input coupler is provided in a first area of the multi-layer structure, and the output coupler is provided in a second area of the multi-layer structure. A dielectric film may be formed on the metal film and may be configured to protect the metal film.

SUMMARY OF THE INVENTION

The present invention seeks to provide an optical assembly which is particularly suited for applications involving direct and prolonged contact with a fluid which over time adversely affects the optical properties and the lifetime of the optical assembly, which is e.g. the case for an implantable optical assembly. In a further aspect the present invention seeks to provide an optical assembly which is particularly suited for applications involving photonic integrated circuits. Photonic integrated circuits as such are known by the skilled person in the field.

According to the present invention, an optical assembly as defined above is provided, further comprising a protective layer covering at least an optical interaction area. The optical interaction area is in direct and prolonged contact with a fluid during operation, e.g. when the optical assembly is embodied as an implantable optical sensor. The protective layer effectively shields the optical interaction area, and more specifically protects the optical microstructure of the optical assembly, from deterioration during use without adversely influencing its optical properties such as refractive index, absorption, etc. The embodiments of the protective layer as presented herein enable interaction of the optical microstructures with the environment of the optical assembly, without changing the desired optical functionalities, over time. More specifically, even though the protective layer may influence the overall optical properties of the optical assembly somewhat (e.g. the effective refractive index of the waveguide), the influence is small enough for the guiding capabilities of the optical microstructure to be maintained, e.g. with respect to a sensing principle.

In a further aspect, the present invention relates to a method of manufacturing an optical assembly, e.g. an optical assembly according to any one of the embodiments described herein. The method comprises providing a substrate with an integrated optical microstructure forming an optical interaction area and providing a protective layer at least over the optical interaction area. As the protective layer can be applied using deposition techniques which are known as such and are compatible with the manufacturing steps for the other elements of the optical assembly, the method can be implemented as an efficient and cost-effective manufacturing method.

SHORT DESCRIPTION OF DRAWINGS

The present invention will be discussed in more detail below, with reference to the attached drawings, in which FIG. 1 shows a schematic two dimensional cross sectional view of an optical microstructure assembly according to a first embodiment of the present invention;

DESCRIPTION OF EMBODIMENTS

Figure 1:
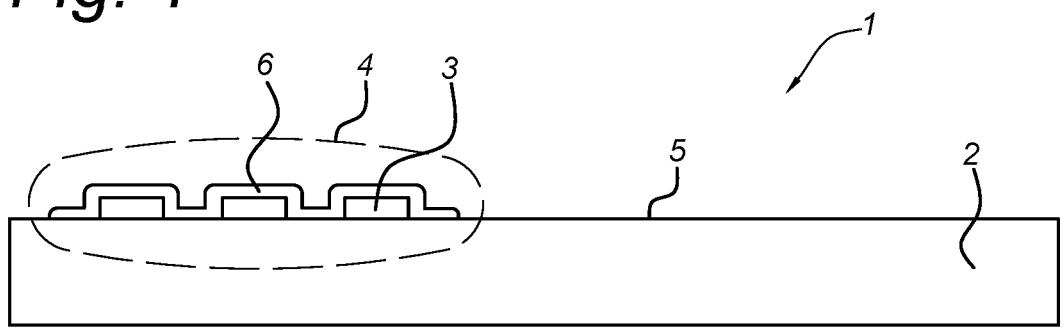

The present invention in general relates to the use of optical microstructures for many applications including an optical assembly which requires direct and/or long term interaction of a surface of the optical microstructure with a hostile environment. These optical structures are configured to guide radiation e.g. via waveguide structures, for which the evanescent tail of the guided radiation is interacting with the environment. FIG. 1 shows a schematic two dimensional cross sectional view of a first embodiment of an optical assembly 1 in accordance with the present invention. The optical assembly 1 comprises a substrate 2 and an optical microstructure 3 integrated with the substrate 2. The optical microstructure 3 is positioned to form an optical interaction area 4 on a part of a surface 5 of the substrate 2. The optical microstructure 3 is e.g. fully or partially embedded, integrated or patterned in the substrate 2 and in direct optical contact with the environment. The optical assembly 1 further comprises a protective layer 6 covering at least the optical interaction area 4. In the embodiment shown in FIG. 1, the optical microstructure 3 comprises a plurality of waveguide structures provided on top of the substrate 2 and covered by the (thin) protective layer 6. As a result, evanescent waves from the optical microstructure 3 can still optically interact with the environment in the optical interaction area 4.

Although most of the light in the optical microstructure 3 is confined within the guiding layer, a small portion, called the evanescent field, extends out into the external medium. The evanescent field is used to interact with the environment for e.g. trapping, sensing, exciting. This evanescent field falls off exponentially as the distance from the waveguide surface increases. E.g. in the case of a sensing application, the variation of the evanescent tail of the optical mode changes the effective refractive index of the guided mode or its amplitude, which can respectively be used as a means for sensing; called evanescent field sensing.

Corrosion is a chemical-physical process in which a material in an initial chemical composition undergoes a chemical reaction with a secondary element from an adjacent material or the surrounding environment (solid, liquid, gaseous or combination of all) thus reducing its enthalpy or thermodynamically available energy (Gibb's free energy) under given ambient conditions (pressure, volume, temperature). The resulting compound is mostly less chemically active than the original material state (chemically inert to the given environmental conditions). If the compound formation is continuous, corrosion will eventually degrade the initial properties of the initial material. The driving force can be initiated either from the material or from its environment or from the combination. From an energy point of view, a system (e.g. a material or material composition) strives towards a minimal free energy, undergoing reactions with its environment towards a product that exhibits a lower free energy than the educts in the system. The reaction product during a corrosion reaction is of different chemical but also of different physical properties compared to its individual educts. For example, a metal that undergoes oxidation reduces its energy to a less chemically active metal-oxide. This involves a change in its underlying quantum structure, leading to a change in band gap and to its properties such as conduction, thermal and chemical behaviour. The reaction has also an impact on the crystallographic structural configuration of the material, leading to a change in its volume upon the chemical reaction. This reaction induces mechanical forces which are exerted on the new material and on adjacent layers, e.g. the initial surface. If the volume of the corrosion product is much larger than the surface area of the educts undergoing the reaction, the stress will accumulate until it induces cracks in the system, releasing the inbuilt stress and so reducing the stored energy. Examples of undergoing a chemical-physical change in order to reduce its energy are flaking of an oxidized material, pitting corrosion, stress crack corrosion, contact corrosion, etc.

A hostile environment, in the sense of the above definition of corrosion, is one that in a liquid, solid or gaseous form contains chemical elements in a state with energy that is capable of inducing corrosion on a material exposed to this environment. Pure water, as an example has a high thermodynamic activity which is reduced through the incorporation of solutes into the liquid matrix. Water can thus be considered a hostile or corrosive environment for materials such as silicon oxide ($SiO_x$) or silicon nitride (SiN). Bodily fluids, containing dissolved oxygen, hydrogen peroxide, chlorine, and multiple other highly oxidizing and other thermodynamically active agents represent an environment that subjects multiple materials to high risk of corrosion.

Hostile environments include, but are not limited to exposure to body tissues and fluids (such as blood or interstitial fluid), in-vitro and in-vivo, vegetal tissues and fluids, fluids in chemical processes such as fermentation tanks and bio reactors, aquacultures including sea, lakes, rivers and aqua tanks and petrochemical fluids, water and corrosive gases. The interaction with a hostile environment will degrade the optical, mechanical and electrical performance of the exposed surface of the optical microstructure, e.g. by corrosion or dissolution. As an example, optical grade silicon (Si) and SiN structures used to transport light through photonic microsystems dissolve, pit and disintegrate when used in aqueous or aggressive chemical environments. In applications where the light from the photonic microsystems is intended to interact with the environment, the deterioration of the surface's quality has a direct impact on the performance of the optical assembly. It is also known that optical microstructures configured for evanescently contacting the environment are heavily impacted by the surface conditions of the optical microstructures. Therefore a protective layer is added in the present invention embodiment, as described in more detail below, which protects the interaction area which has direct interaction with the environment. This coating does not deteriorate the performance of the optical microstructures, nor modifies the functionality of the optical microstructure, as it could be expected by persons skilled in the art. Specifically for an optical assembly it is desired that this protective layer does not adversely affect the desired optical functionalities of the system.

A corrosion resistant material as used in this description refers to a material, which under specific physical environmental conditions (temperature, volume, pressure) either has a state of minimum energy that cannot be further minimized by undergoing a detrimental reaction (oxidation) with the surrounding environment (e.g. solid, gas or liquid); or exhibits a strong intra-material bond, that the thermodynamic activity or chemical potential of the environment cannot disrupt, unless further energy is added into the system. The strength of the system can be given by the level of crystallinity (reduced energy) and its strong intermaterial bonds (present in for example Diamond, Diamond-like carbon (DLC)), the reduced energy and strong bond through preceded by oxidation (e.g. Aluminium oxide ($Al_2O_3$), Titanium oxide) or the combination of both (e.g. Sapphire, pure crystal $Al_2O_3$).

The optical microstructure 3 of the present invention optical assembly embodiments can be implemented as part of a Photonic Integrated Circuit (PIC), which refers to a variety of forms and material systems used for making a photonic circuit. In one embodiment of the present invention, the optical assembly 1 comprises at least one photonic integrated circuit device. In a further embodiment of the present invention, the optical microstructure 3 is based on platforms such as Silicon-on-Insulator (SOD, SiN (silicon rich or stoichiometric silicon), InP, $TiO_2$ semiconductor membranes, polymer, glass/silica, $Al_xGa_{1-x}As$, $In_xGa_{1-x}As_yP_{1-y}$ and plasmonic (e.g. metal nano-particles, metal layers). The optical microstructure 3 can be an integrated optical component, such as an integrated optical cavity, an integrated optical resonator, an integrated optical interferometer, an integrated optical coupler, an optical waveguide, a taper, a tuneable filter, a phase-shifter, a grating, a photonic crystal, a modulator, a detector, a source, a multiplexer, a demultiplexer or a combination thereof, embedded, integrated or patterned in the substrate 2. The optical microstructure 3 can be either active or passive. The optical microstructure 3 is integrated with the substrate as fully embedded or partially embedded structure, in order to form the optical interaction area 4 on the part of the substrate 2. The reference made to the thickness of the optical microstructure in the present description refers to the thickness of its guiding layer (e.g. the thickness of the device layer (Si) in the case of a SOI optical waveguide), thus excluding the thickness of the substrate 2.

The present invention embodiments, such as the one shown in FIG. 1, allows to obtain a surface protection using the protective layer 6 that maintains the capability of optical interaction between the optical microstructure 3 and the external environment of the optical assembly 1. The protective layer 6, of which exemplary embodiments are discussed below, enable optical interaction of the optical microstructure and the environment without changing the desired optical functionalities over time. Fabrication of the optical assembly 1 can be executed using various techniques, such as electron beam technology, photolithographic process, CMOS technology or using silicon based technology, or a combination thereof. This can include material etching processes (e.g. wet etching, dry etching) and other typical back-end-of-line processes (e.g. metallization) or steps involving a heterogeneous integration of other micro-components on the substrate (e.g. flip-chipping, bonding) which are as such known to the person skilled in the art.

Figure 2:
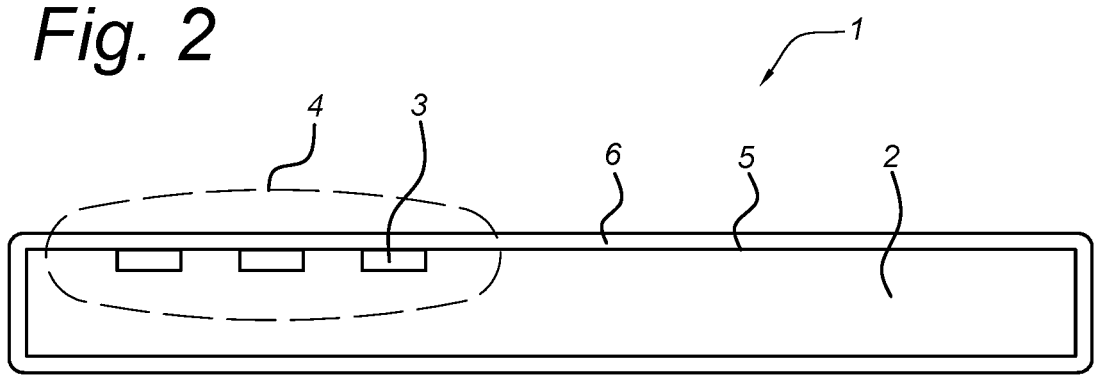
FIG. 2 shows a schematic two dimensional cross sectional view of an optical microstructure assembly according to a second embodiment of the present invention.

FIG. 2 shows a schematic two dimensional cross sectional view of an optical assembly 1 according to a second embodiment of the present invention. In this embodiment, the optical microstructure 3 is embedded in the substrate 2, and the optical interaction area 4 as a result is planar, and level with the surface 5. Furthermore, the protective layer 6 in this embodiment is present on the entire (top) surface 5 of the substrate 2, and even extends onto a back side of the substrate 2. This may be advantageous in view of the processing steps for applying the protective layer 6. Also variations of the embodiments shown in FIG. 1 and FIG. 2 are possible, e.g. with the protective layer 6 present over the entire surface 5 (including front side, back side and edges in between the front side and back side. It is noted that for a proper operation of the optical assembly 1 in a hostile environment, presence of the protective layer 6 over the optical interaction area 4 is sufficient. The remaining part of the optical assembly 1 is then not necessarily covered with the protective layer 6.

In a further embodiment of the present invention the protective layer 6 is conformal to an external surface associated with the optical interaction area 4. A conformal layer implementation of the protective layer 6 covers all surfaces with a coating of a substantially uniform thickness which means that the thickness of the conformal protective layer 6 will be substantially same over the entire optical interaction area 4 where the protective layer 6 is present. An example of a deposition method for conformal coating is Atomic Layer Deposition (ALD) (e.g. Thermal ALD or plasma-enhanced ALD). The external surface associated with the optical interaction area 4 spans across the optical microstructure 3 which is e.g. patterned or embossed in the surface 5. For a patterned optical interaction area 4, the conformal protective layer 6 covers the steps, corners and curves of the optical microstructure 3 in a substantially uniform manner (as shown in the embodiment of FIG. 1). In an even further embodiment of the present invention, the protective layer 6 comprises a material with corrosion-protection characteristics. Thus the protective layer 6 will protect the optical microstructure 3 (and surrounding parts of the surface 5 in the optical interaction area 4) against deterioration (corrosion and dissolution) when exposed to a corrosive hostile environment.

To allow evanescent field sensing, the protective layer 6 is selected in such a manner that it does not adversely affect the optical properties of the optical microstructure 3. In a further embodiment of the present invention, the protective layer 6 is one or more materials from the group of Silicon Carbide (SiC), Diamond Like Carbon (DLC), $TiO_2$, or $Al_2O_3$. DLC is also known in the art as a metastable form of amorphous carbon. Each of these materials, with the exception of DLC, are dielectric in nature and can be deposited on optical microstructures with a controlled thickness. The usage of SiC (mainly in its amorphous form (a-SiC)), $TiO_2$ and $Al_2O_3$ as a protective layer 6 has advantages due to its compatibility and ease of integration with Si and Si-based microfabrication technologies which are applied for the optical assembly 1. Additionally, properties such as inertness, long lasting mechanical stability, bio compatibility and optical compatibility make it a good candidate for using as a protective layer 6 on the present invention embodiments. DLC type of a protective layer 6 provides a very good chemical inertness against strong oxidising agents which are for example used in paper bleaching industry or in waste water treatment plants. Furthermore, although these materials are known for being poor optical waveguides, applying just a thin coating ensures that the protective layer 6 does not adversely change the light propagation in the underlying waveguide of the optical microstructure 3. The protective coating materials are compatible with a possible selection of the material of the optical microstructure 3 as main light-carrying means, from the group of high quality optical grade materials such as Si, SiOx, SiN and III-V materials. As a result, the present invention embodiments allow protection of mono-modal photonic waveguides as implementations of the optical microstructure 3 without deterioration of the optical properties.

Optical grade Si and SiN waveguides which are used to transport light through optical microstructures 3 dissolve, pit and disintegrate when used in aqueous or aggressive chemical environments. In applications where the light in the optical microstructure 3 interacts with the environment e.g. a sensing activity, the deterioration of the quality of the optical microstructure 3 and the associated optical interaction area 4 has a direct impact on the performance of the optical assembly 1. The substance exposed to the optical assembly 1 may be a target analyte for a sensor, the analyte being present in for example in tissue, bodily fluid such as interstitial fluid, urine or blood, etc. Alternatively, the optical assembly 1 may be used to sense presence of a chemical fluid when referring to the operation of the optical assembly 1 in e.g. a fermentation tank, in a fuel tank or in fuel pipeline which is typically used in for example in a petrochemical environment. As discussed above, the protective layer 6 enables optical interaction of the optical microstructure 3 with the environment without changing its structural, physical, optical or chemical properties over time. Due to this reason polymer layers which are susceptible to chemical or biological degradation, or those which would affect the optical properties of the sensor are not chosen as a protective layer 6. All other areas of the device could, but must not be, protected with a polymer.

In an even further embodiment of the present invention, the protective layer 6 is non-porous, e.g. the protective layer 6 comprises a material which is non-porous in nature. This embodiment prevents occurrence of porosity channels or pin holes in the protective layer 6 which would allow a chemical or biological fluid to make a direct contact with the optical microstructure 3 during operation, thereby degrading the material and optical performance of the optical assembly 1. By having a non-porous protective layer 6, any direct exposure of the optical interaction area 4 with a hostile sensing environment is prevented, even after a long term operational use.

Evanescent field sensing utilises optical microstructures 3 supporting both single mode and multimode wave propagation. Multimode optical microstructures 3 have a thickness greater than the wavelength of the light used for absorption by the compound to be measured. However, due to relatively low levels of evanescent field intensity, detection methods are limited for sensing applications. Single mode waveguides typically comprise a very thin (less than the wavelength of the light) high dielectric index core deposited on a low index cladding. The films are typically fabricated using thin film deposition techniques or epitaxial growth. Single mode waveguides with large index differences between the core and the cladding (high contrast waveguide systems) offer greater sensitivity due to the high field intensity at the surface. Single mode planar waveguides with high index contrast enable a rapid decay of the evanescent field away from the waveguide surface with no appreciable intensity beyond one-half the wavelength of the light (~250 nm-300 nm), while low contrast mono-mode and multi-mode configurations typically exhibit a penetration depth of 1-2 µm. The protective layer 6 has a thickness which is equal to or less than 50% of the optical microstructure 3 (e.g. an optical waveguide) in an even further embodiment. The thickness can be even smaller such as less than 30% or even less than 10%. The protective layer 6 has been chosen to be equal to or less than 50% as a thicker layer could possibly affect the accessibility of the sensing media to the optical evanescent field in the first place and deteriorate the overall optical behaviour substantially in the second place. Due to the limited distance in which the evanescent field exists in an optical microstructure 3, the protective layer 6 is advantageously as thin as possible.

The propagation of the guided wave in the optical microstructure 3 can be either a transverse-electric (TE) polarized guided wave or a transverse-magnetic (TM) polarized guided wave. A TE wave has its electric field vector parallel to the surface of the planar waveguide and for a TM wave has its electric field vector perpendicular to the planar waveguide surface. The overall sensitivity of an optical microstructure 3 depends strongly on the waveguide material and its design. Specifically, optimizing the overlap of the exponentially decaying electric field with thickness of the protective layer 6 and maximizing the electric field strength at the waveguide surface, can optimize detection sensitivity of the optical assembly 1. In practice, a thin, protective layer 6 leads to have a high amount of evanescent field outside the optical microstructure 3 compared to a thicker protective layer 6. The protective layer 6 can be applied to any type of optical microstructure 3, irrespective of which polarised guided wave the optical microstructure 3 supports. The advantage of using a thin anti-corrosive protective layer 6 is that it allows optical interaction of the entire waveguide of the optical microstructure 3 with its environment without surface deterioration thereof, and as a result a high longevity in a biological or other corrosive environment.

In an exemplary embodiment, the optical microstructure 3 is a waveguide spiral of certain length (typically the optimum length for maximal interaction with analyte in the cladding region) exposed to the environment. The light is guided by the spiral waveguide, configured to have the evanescent tail of the guided modes or mode overlapping the environment. The interaction of the light with the environment will impact the spectral amplitude of the light.

In an exemplary embodiment, the optical microstructure 3 is a micro-ring resonator (MRR), a compact wavelength selective device. In the case of a three port MRR, three ports are provided which are known as 'In port' (coupling in light), 'Through Port' (coupling out light) and 'Drop port' (coupling out light). When an optical signal passes through the 'In port' of a MRR, a part of the optical signal is evanescently coupled into the cavity which propagates around the ring and interferes with a later arriving part of the incoming signal from the 'In port'. Destructive interference (of the cavity field and the field of the incoming signal) results in passing most of the light to the 'Through port' and constructive interference will result in most of the input power to circle the ring and eventually appear in the 'Drop port', again through evanescent coupling. In other words, light around resonant wavelengths appears as peaks in the 'Drop port' and as dips in the 'Through port'. The resonant wavelengths of the MRRs are highly affected by a change in its evanescent field which is utilised for using it as a strong evanescent field optical for biological and chemical applications. More general, depending on the loss of the system (propagation loss and coupling loss) the light stays inside and goes around the ring for 'N' number of times as determined by the quality factor of the ring. This on one hand effectively increases the interaction with the analyte and on the other hand is also extremely sensitive to any small change in the surrounding environment.

In an exemplary embodiment, the optical microstructure 3 is a guiding structure based on a slot waveguide. A slot waveguide comprises two arms of high refractive indices separated by a slot region of low refractive index. In optical slot waveguides (e.g. fabricated in SOI technology by either e-beam or deep-UV lithography) the electric field discontinuity at the interface between high index contrast materials enables high optical confinement inside a nanometer scale area (gap region) of low-index material. A variety of optical microstructures can be realized using slot waveguides such as spiral waveguides, micro-ring resonators, disk resonators and one dimensional photonic crystals. The very high field intensity build up in the slot region combined with the effective refractive index of the slot guiding structure is very sensitive to changes in the refractive index of its environment making it an efficient optical sensor.

Figure 3:
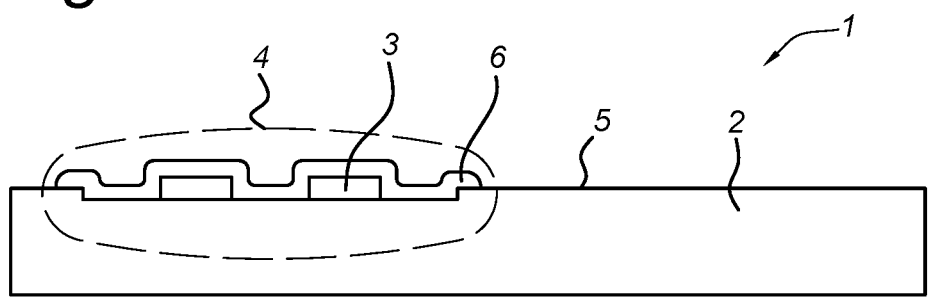
FIG. 3 shows a schematic two dimensional cross sectional view of an optical microstructure assembly according to a third embodiment of the present invention.

FIG. 3 shows a schematic two dimensional cross sectional view of an optical assembly 1 according to a further embodiment of the present invention. In this embodiment, the optical microstructure 3 is etched in the substrate 2 and the optical interaction area 4 as a result is a patterned valley in the surface 5. The protective layer 6 in this embodiment is conformal to the etched valleys and to the surface 5 of the optical microstructure 3.

Figure 4:
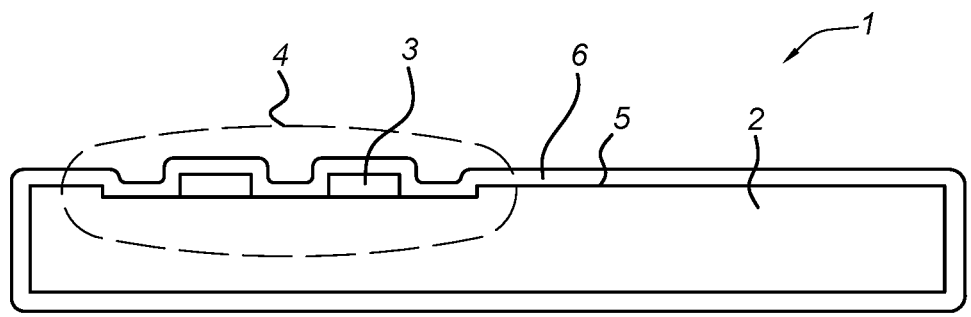
FIG. 4 shows a schematic two dimensional cross sectional view of an optical microstructure assembly according to a further embodiment of the present invention.

In an even further embodiment, the protective layer 6 extends onto the back and edge sides of the substrate 2. This may be advantageous in view of the processing steps for applying the protective layer 6. FIG. 4 shows a schematic two dimensional cross sectional view of an optical assembly 1 according to this embodiment of the present invention. Similar to the embodiment shown in FIG. 3, here the optical microstructure 3 is etched in the substrate 2 and the optical interaction area 4 as a result is a patterned valley in the surface 5.

The protective layer 6 is optically transparent (low optical losses) in a further embodiment of the present invention. In a further embodiment, it can be transparent in a visible wavelength region or an infrared (IR) region of the electromagnetic spectrum. This can be in the near IR wavelength range (between 700 nm and 2500 nm) or in the mid IR wavelength range (2.5 µm to 8 µm). The optical assembly 1 may be adapted for use in those wavelength regions where for example, glucose has particular absorption peaks or scattering resonances. For example, the optical assembly may be adapted for operating in the first-overtone band (1500 nm to 1850 nm) and/or the combination band (2080 nm to 2325 nm) where glucose has numerous absorption bands and water has relatively lower absorption. The selection of which wavelength range is used could for example also be based on the available radiation sources.

The reference made to light or radiation in the present application refers to electromagnetic radiation. The light envisaged is radiation having a suitable wavelength or wavelength range for sensing, i.e. detecting or imaging, a substance. In some embodiments light used will be visible radiation or IR radiation, e.g. near IR radiation or mid IR radiation. In some embodiments, the radiation has a wavelength or wavelength range between 700 nm and 2500 nm, or between 2.5 µm and 8 µm, or a combination thereof, although the present invention embodiments are not limited thereto. For example the fabrication and integration technologies for the silicon photonics are well developed in the telecommunication wavelength range which is centred around 1550 nm, which could be exploited for easy, reliable and cost-effective manufacturing of the present invention optical assembly 1.

Figure 5:
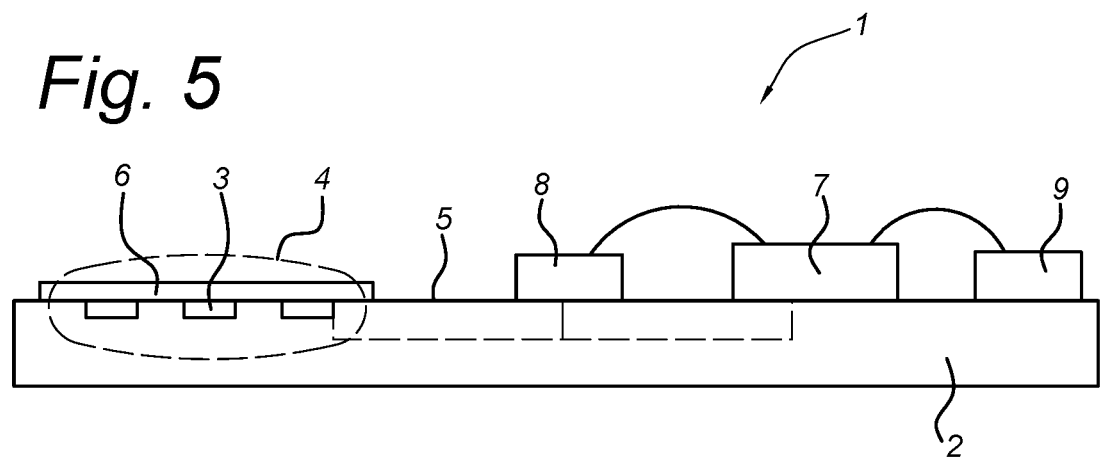
FIG. 5 shows a schematic representation in cross sectional view of an even further embodiment of the optical assembly of the present invention.

FIG. 5 shows a schematic representation in cross sectional view of an even further embodiment of the optical assembly 1 of the present invention. In this embodiment the optical assembly 1 comprises processing circuitry 7 attached to or integrated in the substrate 2. A radiation source 8 and a detector are connected to the processing circuitry 7. An interfacing circuitry 9 (e.g. an electronic circuitry) is connected to the processing circuitry 7, the at least one radiation source 8 and the detector. The optical assembly 1 in this embodiment is e.g. an implantable sensor, a (partially) immersed sensor, or a floating sensor), the processing circuitry 7, the radiation source 8, the at least one detector and/or interfacing circuitry 9 (wired or wireless) in operation being arranged for optical sensing of a substance in contact with the optical interaction area 4. The protective layer 6 covers the optical interaction area 4 of the optical assembly 1. Detectors may be integrated in the optical assembly 1 to convert the optical signals into electrical signals. The detector can be a part of the processing circuitry 7 or can be arranged as a separate device. After processing the processed radiation at processing circuitry 7, an output signal may be generated via the interfacing circuitry 9. The interfacing circuitry 9 facilitates the transmission of data and power in and out of the optical assembly 1.

As shown in FIG. 5, the radiation source 8 and interfacing circuitry 9 are electrically connected to and controlled by the processing circuitry 7, while the radiation source 8 and detector are in optical communication with the optical microstructure 3. The processing circuitry 7 is e.g. implemented as a photonic integrated circuit and is arranged for spectrally controlling radiation emitted from the radiation source 8 whose radiation is used for e.g. sensing a substance, and for processing the sensing signals (optically or electronically). The processing circuitry 7 may comprise electronics or fluidic circuitry which is monolithically, hybrid or heterogeneously integrated within the optical assembly 1. In other words, the optical assembly may be arranged for capturing radiation that was directed from the radiation source 8 and that has interacted with the substance in contact with the optical interaction area 4 of the optical microstructure 3. The processing circuitry 7 may comprise a plurality of integrated components, such as waveguides, multiplexers, demultiplexers, couplers, splitters, filters and even tuneable elements. The processing circuitry 7 is adapted for processing the radiation in a wavelength dependent manner. In at least some embodiments of the present invention the processing circuitry 7 may comprise optical components. The processing circuitry 7 for example act as a multiplexer or demultiplexer or part thereof, an interferometer or part thereof, an integrated optical cavity, an integrated optical resonator, an integrated optical coupler, a waveguide, a grating, or a combination thereof. The processing circuitry 7 may for example comprise a coupler for coupling and decoupling the radiation in and out of the chip. One example of a coupler may be an on-chip diffraction grating. The couplers capturing the radiation on the chip may be optimized for capturing the optimum amount of light, using optical design techniques. The processing circuitry 7 may be an interferometer, a tuneable filter, an arrayed waveguide grating (AWG), a planar concave grating (PCG) or a combination thereof. It is an advantage of this embodiment that photonic integrated circuit based radiation processors may be used as processing circuitry 7 allowing miniaturization of the optical assembly 1. The miniaturization enables the device to be so compact that the natural flow of bodily fluids or the natural diffusion of substance, e.g. present in living creatures, enables the possibility for sensing and for continuous monitoring of the substance. It is also an advantage for e.g. that sensing is performed using optical characterization, therefore not requiring reagents or other auxiliary substances. These advantages result in a reliable and long term usable optical assembly 1, without the need for significant user interaction.

Figure 6:
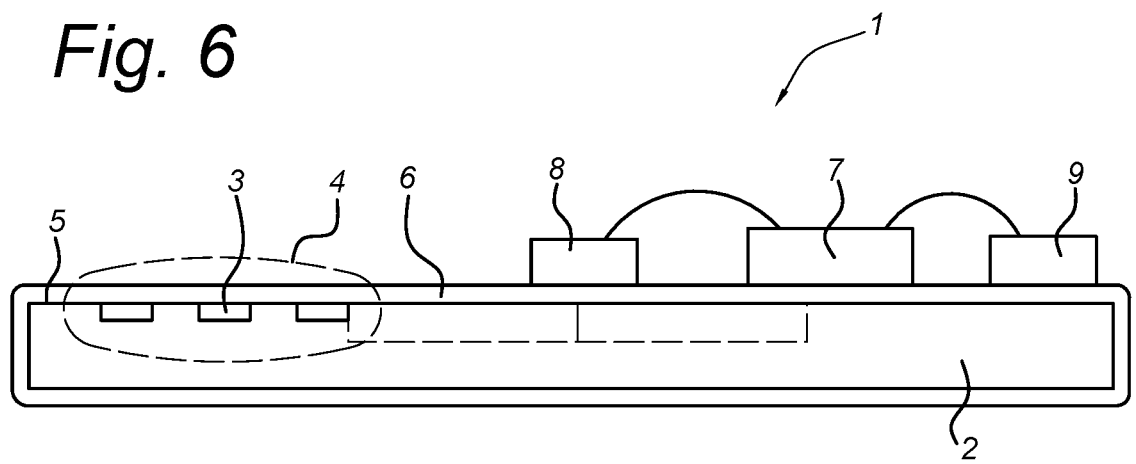
FIG. 6 shows a schematic representation in cross sectional view of an even further embodiment of the optical assembly of the present invention.

FIG. 6 shows a schematic representation in cross sectional view of an even further embodiment of the optical assembly 1 of the present invention. In this embodiment the optical assembly 1 comprises processing circuitry 7 attached to or integrated in the substrate 2; with a radiation source/detector 8 being connected to the processing circuitry 7. An interfacing circuitry 9 is connected to the processing circuitry 7 and the radiation source/detector 8. In this embodiment, the protective layer 6 covers all the surfaces of the substrate 2 of the optical assembly 1.

In an alternative or additional embodiment, the optical microsystem assembly 1 is an implantable sensor. The sensor can be for the sensing of a substance in the body of living creatures including the human being, but the invention is not limited thereto. The living creature may be any creature wherein the sensor can be implanted. It may for example be a plant or an animal, such as a mammal or non-mammal. It may be cold-blooded or warm-blooded. In some preferred embodiments, sensors are provided for sensing glucose, although also sensors are provided for sensing of other substances, such as urea, lactate, creatinine, triglyceride, protein, cholesterol, and ethanol. Alternatively or in addition thereto, the substance thus also may include tissue itself and sensing may be performed for imaging purposes, e.g. blood vessels, nerves, cancer tissue, cellular changes, etc. It is to be noticed that the wavelength at which sensing is performed mainly may be determined by the substance to be sensed. The selection of a different substance to be sensed, i.e. detected, imaged or monitored, thus may result in the need for using similar components as described for glucose, but having operability in another wavelength region or converters therefore. For the sake of convenience, embodiments of the present invention will be further described with reference to glucose sensing, but it will be clear to the person skilled in the art that the description in the embodiments and examples is mutates mutandis applicable to embodiments of substance sensing in a different wavelength or of a different substance. The sensor may be adapted for example by a particular detecting element and/or radiation source as well as by optical components used in the optical processor, to be used in a the near IR radiation wavelength range, e.g. in a range between 700 nm and 2500 nm.

The photonic and/or electronic components of the optical assembly 1 can be integrated for example monolithically, heterogeneously or by a hybrid method. Monolithic integration is the integration technology that uses a single processing flow to process the diverse components potentially using different materials, e.g. epitaxial grown germanium detectors in silicon photonics Integrated Circuit (IC). Heterogeneous integration is the integration technology for which the components are processed in separate process flows, which are then integrated at die or wafer level, e.g. BCB bonding, wafer bonding, other bonding schemes or 3D integration. Hybrid integration is the integration of components or materials on processed photonic integrated platforms, e.g. flip-chipping of detectors, bumping, gluing, wire bonding, co-packaging, etc.

The devices and methods of the present invention embodiments are described for a wide range of materials including Si, Si compatible materials, III-V materials, polymers, SiN/SiOx. In an exemplary embodiment, the present invention relates to an embodiment wherein the optical assembly 1 is a SiN based material implementation. SiN is a very interesting material implementation for highly integrated photonic circuits. The high refractive index contrast allows photonic waveguides and waveguide components with submicron dimensions to guide, bend and control light on a very small scale so that various functions can be integrated on a small chip.

SOI based optical microstructures 3 allow a high level of miniaturization, which is advantageous. Furthermore light can be efficiently coupled in and out the optical microstructure 3 by use of e.g. a grating coupler or another coupling element. Using SOI also has some technological advantages. Due to the CMOS industry, silicon technology has reached a level of maturity that outperforms any other plane chip manufacturing technique by several orders of magnitude in terms of performance, lithographical precision, reproducibility and throughput. Nano-photonic ICs can be fabricated with wafer scale-processes, which means that a wafer can contain a high number of photonic integrated circuits. Combined with the commercial availability of large wafers at a relative moderate cost, this means that the price per optical assembly 1 can be very low.

The present invention in a further aspect relates to a method for manufacturing an optical assembly, e.g. an optical assembly 1 according to any one of the embodiments described herein, the method comprising providing a substrate 2 with an integrated optical microstructure 3 forming an optical interaction area 4, and providing a protective layer 6 at least over the optical interaction area 4. As discussed above, the protective layer 6 may be provided conformal to an external surface of the optical interaction area 4, for which the processing alternatives as discussed above may be advantageously used. The deposition techniques used (especially for depositing the protective layer 6) may be selected to enhance or optimize one or more of the protective layer 6 characteristics. In an alternative embodiment, the deposition method may be optimized to have the protective layer 6 provided as a non-porous layer.

The method of applying the protective layer 6 may be using one of many thin film fabrication technologies which are known as such. For example this can be Chemical Vapour Deposition (CVD), Plasma Enhanced Chemical Vapour Deposition (PECVD), Atomic Layer Deposition (ALD), sputtering, pulsed laser deposition (PLD) or a Molecular Beam Epitaxy (MBE) deposition technique. When using a PECVD method, it is possible, but not restricted to the use of silane and methane as main gases for depositing SiC or a DLC layer as protective layer 6 on top of the optical microstructure 3 without affecting its optical transparency and further optical characteristics. The protective layer 6 can be deposited and structured using identical methods of manufacturing as are used for manufacturing the optical microstructure 3 (e.g. structured and patterned by photolithography and dry reactive etching methods).

The present invention has been described above with reference to a number of exemplary embodiments as shown in the drawings. Modifications and alternative implementations of some parts or elements are possible, and are included in the scope of protection as defined in the appended claims.

The invention claimed is:

1. An implantable optical sensor comprising a substrate and at least one optical microstructure for evanescent field sensing integrated with the substrate, the at least one optical microstructure being positioned to form an optical interaction area on a part of a surface of the substrate, the optical sensor further comprising a protective layer covering at least the optical interaction area, the protective layer being in a predetermined material with corrosion-protection characteristics and having a predetermined thickness, so as not to affect the evanescent field sensing, wherein the protective layer is compatible with a possible selection of the material of the optical microstructure as main light-carrying means, from the group of high quality optical grade materials comprising at least one of Si, SiOx, SiN and III-V materials, and wherein the protective layer has a thickness of less than 50% of a thickness of the optical microstructure, wherein the protective layer covers steps, corners and curves of the at least one optical microstructure in a conformal manner.

2. The implantable optical sensor according to claim 1, wherein the protective layer comprises one or more materials from the group of: Silicon Carbide (SiC), Diamond Like Carbon (DLC), $TiO_2$, $Al_2O_3$.

3. The implantable optical sensor according to claim 1, further comprising at least one photonic integrated circuit device.

4. The implantable optical sensor according to claim 1, wherein the optical microstructure is based on SiN, SOI, InP, GaAs, $TiO_2$, glass or silica.

5. The implantable optical sensor according to claim 1, wherein the protective layer is non-porous.

6. The implantable optical sensor according to claim 1, wherein the protective layer has a thickness of less than 30% of a thickness of the optical microstructure.

7. The implantable optical sensor according to claim 1, wherein the protective layer has a thickness of less than 10% of a thickness of the optical microstructure.

8. The implantable optical sensor according to claim 1, wherein the at least one optical microstructure is configured for evanescent field sensing with light in a predetermined wavelength range.

9. The implantable optical sensor according to claim 8, wherein the substrate is a cladding and the optical microstructures are single mode waveguides comprising a core deposited on the cladding, the core having a thickness less than the wavelength of the light and having a refractive index higher than the refractive index of the cladding.

10. The implantable optical sensor according to claim 8, wherein the wavelength of the light is in the near IR wavelength range, between 700 nm and 2500 nm, or in the mid IR wavelength range, between 2.5 μm and 8 μm.

11. The implantable optical sensor according to claim 8, wherein the wavelength of the light is in a band from 1500 nm to 1850 nm or in a band from 2080 nm to 2325 nm.

12. The implantable optical sensor according to claim 1, wherein the protective layer is optically transparent.

13. The implantable optical sensor according to claim 1, wherein the sensor comprises processing circuitry integrated in the substrate and connected to the optical microstructure; a radiation source connected to the processing circuitry and to the optical microstructure; and interfacing circuitry connected to the processing circuitry; the processing circuitry and radiation source in operation being arranged for optical sensing of a substance interacting with an evanescent field associated with the optical microstructure and the optical interaction area.

14. A method of manufacturing an implantable optical sensor, the method comprising:

providing a substrate;

integrating at least one optical microstructure for evanescent field sensing with the substrate, the at least one optical microstructure being positioned to form an optical interaction area on a part of a surface of the substrate);

providing a protective layer at least over the optical interaction area, the protective layer being in a predetermined material with corrosion-protection characteristics and having a predetermined thickness, so as not to affect the evanescent field sensing, and wherein the provided protective layer is compatible with a possible selection of the material of the optical microstructure as main light-carrying means, from the group of high quality optical grade materials comprising at least one of Si, SiOx, SiN and III-V materials, wherein the protective layer covers steps, corners and curves of the at least one optical microstructure in a conformal manner.

15. The method according to claim 14, wherein the protective layer is provided using a chemical vapour deposition (CVD), a plasma enhanced chemical vapour deposition (PECVD), an atomic layer deposition (ALD), a sputtering, or a molecular beam epitaxy deposition technique.

16. The method according to claim 14, wherein the protective layer is compatible with a possible selection of the material of the optical microstructure as main light-carrying means, from the group of high quality optical grade materials comprising at least one of Si, SiOx, SiN and III-V materials, and wherein the protective layer has a thickness of less than 50% of a thickness of the optical microstructure.

* * * * *